United States Patent
Bolli et al.

(10) Patent No.: US 9,617,250 B2
(45) Date of Patent: Apr. 11, 2017

(54) PYRIDIN-4-YL DERIVATIVES

(71) Applicant: ACTELION PHARMACEUTICALS LTD., Allschwil (CH)

(72) Inventors: Martin Bolli, Allschwil (CH); Cyrille Lescop, Allschwil (CH); Oliver Nayler, Allschwil (CH); Beat Steiner, Allschwil (CH)

(73) Assignee: ACTELION PHARMACEUTICALS LTD., ALLSCHWIL (CH)

( * ) Notice: Subject to any disclaimer, the term of this patent is extended or adjusted under 35 U.S.C. 154(b) by 0 days.

(21) Appl. No.: 14/777,444

(22) PCT Filed: Mar. 14, 2014

(86) PCT No.: PCT/IB2014/059794
§ 371 (c)(1),
(2) Date: Sep. 15, 2015

(87) PCT Pub. No.: WO2014/141171
PCT Pub. Date: Sep. 18, 2014

(65) Prior Publication Data
US 2016/0031866 A1 Feb. 4, 2016

(30) Foreign Application Priority Data
Mar. 15, 2013 (EP) .................................. 13159482

(51) Int. Cl.
C07D 413/04 (2006.01)

(52) U.S. Cl.
CPC .................. C07D 413/04 (2013.01)

(58) Field of Classification Search
CPC .................................................. C07D 413/04
USPC ........................................ 546/269.4; 514/340
See application file for complete search history.

(56) References Cited

U.S. PATENT DOCUMENTS

| | | | |
|---|---|---|---|
| 8,044,076 B2 | 10/2011 | Bolli et al. |
| 8,288,554 B2 | 10/2012 | Bolli et al. |
| 8,299,086 B2 | 10/2012 | Bolli et al. |
| 8,410,151 B2 | 4/2013 | Bolli et al. |
| 8,575,200 B2 | 11/2013 | Bolli et al. |
| 8,580,824 B2 | 11/2013 | Bolli et al. |
| 8,592,460 B2 | 11/2013 | Bolli et al. |
| 8,598,208 B2 | 12/2013 | Bolli et al. |
| 8,658,675 B2 | 2/2014 | Bolli et al. |
| 9,133,179 B2 | 9/2015 | Bolli et al. |
| 2011/0028448 A1 | 2/2011 | Bolli et al. |
| 2011/0046170 A1 | 2/2011 | Bolli et al. |

FOREIGN PATENT DOCUMENTS

| WO | WO 91/15583 | 10/1991 |
|---|---|---|
| WO | WO 99/46277 | 9/1999 |
| WO | WO 2004/035538 | 4/2004 |
| WO | WO 2008/029370 | 3/2008 |
| WO | WO 2008/029371 | 3/2008 |
| WO | WO 2008/035239 | 3/2008 |
| WO | WO 2008/114157 | 9/2008 |
| WO | WO 2009/024905 | 2/2009 |
| WO | WO 2009/043889 | 4/2009 |
| WO | WO 2009/057079 | 5/2009 |
| WO | WO 2009/109872 | 9/2009 |
| WO | WO 2009/109904 | 9/2009 |
| WO | WO 2009/109906 | 9/2009 |
| WO | WO 2009/109907 | 9/2009 |
| WO | WO 2010/100142 | 9/2010 |
| WO | WO 2011/007324 | 1/2011 |
| WO | WO 2011/071570 | 6/2011 |
| WO | WO 2012/098505 | 7/2012 |

OTHER PUBLICATIONS

Hu et al., "Sphingosine-1-phosphate, etc.," Mol. Biol. Rep. (2011) 38:4225-4230.*
Van der Giet et al., "Relevance and potential, etc.," Biol. Chem., 389, pp. 1381-1390 (2008).*
Jo et al., "Sphingosine-1-phosphate, etc.," Kidney International (2008) 73, 1220-1230.*
Bode et al., "Immune Regulation, etc.," Arch. Immunol. Ther. Exp. (2012) 60: 3-12.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Simone, Oncology: Introduction, Cecil Textbook of Medicine, 20th Edition, vol. 1, pp. 1004-1010, 1996.*
Robinson, Medical Therapy of Inflammatory Bowel Disease for the 21st century, Eur. J. Surg. 164, Suppl. 582, pp. 90-98, (1998).*
Spiegel et al., Nature Reviews Immunology, vol. 11, No. 6, pp. 403-415, Jun. 2011.*
An et al., "Identification of cDNAs encoding two G protein-coupled receptors for lysosphingolipids", FEBS Letters, vol. 417, p. 279-282, (1997).
Chakraborti et al., "One-Pot Synthesis of Nitriles from Aldehydes Under Microwave Irradiation: Influence of the Medium and Mode of Microwave Irradiation on Product Formation+", Tetrahedron, vol. 55, p. 13265-13268, (1999).

(Continued)

Primary Examiner — Patricia L Morris
(74) Attorney, Agent, or Firm — Hoxie & Associates LLC

(57) ABSTRACT

The invention relates to compounds of the Formula (I), Formula (I) wherein $R^1$ and $R^2$ are as described in the description, their preparation and their use as pharmaceutically active compounds. Said compounds particularly act as immunomodulating agents.

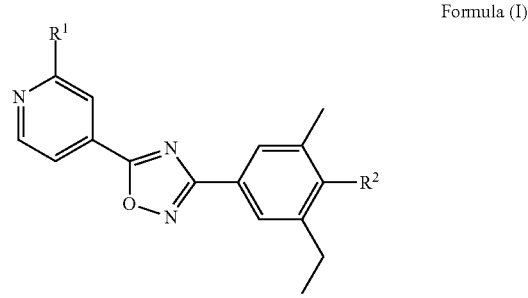

Formula (I)

11 Claims, No Drawings

(56) References Cited

OTHER PUBLICATIONS

Doucet et al., "Suzuki—Miyaura Cross-Coupling Reactions of Alkylboronic Acid Derivatives or Alkyltrifluoroborates with Aryl, Alkenyl or Alkyl Halides and Triflates", European Journal of Organic Chemistry, p. 2013-2030, (2008).
Fryer et al., "The Clinically-tested S1P Receptor Agonists, FTY720 and BAF312, Demonstrate Subtype-Specific Bradycardia (S1P1) and Hypertension (S1P3) in Rat", PLOS One, vol. 7 (12), p. 1-9, (2012).
Furstner et al., "Iron-Catalyzed Cross-Coupling Reactions", Journal of the American Chemical Society, vol. 124, p. 13856-13863, (2002).
Gangloff et al., "Synthesis of 3, 5-disubstituted-1,2,4-oxadiazoles using tetrabutylammonium fluoride as a mild and efficient catalyst", Tetrahedron Letters, vol. 42, p. 1441-1443, (2001).
Gon et al., "S1P$^3$ Receptor-induced reorganization of epithelial tight junctions compromises lung barrier integrity and is potentiated by TNF", PNAS, vol. 102(26), p. 9270-9275, (2005).
Hale et al., "Selecting against S1P3 enhances the acute cardiovascular tolerability of 3-(N-benzyl)aminopropylphosphonic acid S1P receptor agonists", Bioorganic & Medicinal Chemistry Letters, vol. 14, p. 3501-3505, (2004).
Hamada et. al., "Removal of Sphingosine 1-Phosphate Receptor-3 (S1P3) Agonism is Essential, but Inadequate to Obtain Immunomodulating 2-Aminopropane-1,3-diol S1P1 Agonists with Reduced Effect on Heart Rate", J. Med. Chem., vol. 53, p. 3154-3168, (2010).
Hamz et al., "Synthesis of Various 3-Substituted 1,2,4-Oxadiazole-Containing Chiral β3- and -Amino Acids from Fmoc-Protected Aspartic Acid", The Journal of Organic Chemistry, vol. 68(19), p. 7316-7321, (2003).
Hla et al., "An Abundant Transcript Induced in Differentiating Human Endothelial Cells Encodes a Polypeptide with Structural Similarities to G-protein-coupled Receptors", J. Biol Chem., vol. 265(16), p. 9308-9313, (1990).
John et al., "Reactions of (Difluoroamino)difluoroacetonitrile and (Difluoroamino) difluoroacetamidoxime", Inorganic Chemistry, vol. 27, p. 3100-3104, (1988).
Kaboudin et al., "One-pot Synthesis of 1,2,4-Oxadiazoles Mediated by Microwave Irradation Under Solvent-Free Condition", Heterocycles, vol. 60 (10), p. 2287-2292, (2003).
Kerins et al., "Generation of Substituted Styrenes via Suzuki Cross-Coupling of Aryl Halides with 2,4,6-Trivinylcyclotriboroxane", The Journal of Organic Chemistry, vol. 67(14), p. 4968-4971, (2002).
Lucke et al., "Endothelial Functions of Sphingosine-1-phosphate", Cellular Physiology and Biochemistry, vol. 26, p. 87-96, (2010).
Matsushita et al., "Palladium-Catalyzed Reactions of Allylic Electrophiles with Organometallic Reagents. A Regioselective 1, 4-Elimination and a Regio- and Stereoselective Reduction of Allylic Derivatives", The Journal of Organic Chemistry, vol. 47, p. 4161-4165, (1982).
Meyer et al., "Synthesis of New 1,2,4- and 1,3,4-Oxadiazole Derivatives", Synthesis, p. 899-905, (2003).
Murakami et al., "Sphingosine 1-Phosphate (S1P) Regulates Vascular Contraction via S1P3 Receptor: Investigation Based on a New S1P3 Receptor Antagonist", Mol. Pharmacol., vol. 77(4), p. 704-713, (2010).
Poulain et al., "Parallel synthesis of 1,2,4-oxadiazoles from carboxylic acids using an improved, uronium-based, activation", Tetrahedron Letters, vol. 42, p. 1495-1498, (2001).
Remington, The Science and Practice of Pharmacy, "Pharmaceutical Manufacturing" 21st Edition, Part 5, (2005).
Salomone et al., "Analysis of sphingosine 1-phosphate receptors involved in constriction of isolated cerebral arteries with receptor null mice and pharmacological tools", Brit. J. Pharmacol., vol. 153, p. 140-147, (2008).
Srivastava et al., "Synthesis of 3-Aryl-5-[Thien-3-yl Methyl]-1,2,4-Oxadiazoles", Synthetic Communications, vol. 29(9), p. 1437-1450, (1999).
Stahl et al., "Handbook of Pharmaceutical Salts, Properties, Selection and Use", International Union of Pure and Applied Chemistry, (2012).
Suzuki et al., "Synthesis of the Selective 5-Hydroxytryptamine 4 (5-HT4) Receptor Agonist (+)-(S)-2-Chloro-5-methoxy-4-[5-(2-piperidylmethyl)-1,2,4-oxadiazol-3-yl]aniline", Chemistry Pharmaceutical Bulletin, vol. 47(1), p. 120-122, (1999).
Yamaguchi et al., "Molecular Cloning of the Novel Human G Protein-Coupled Receptor (GPCR) Gene Mapped on Chromosome 9$^1$", Biochemical Biophysical Research Communications, vol. 227, p. 608-614, (1996).
International Search Report of International Application No. PCT/IB2014/059794 mailed Jun. 10, 2014, 2 pages.
Furtsner et al., "Eisenkatalysierte Kreuzkupplungen von AlkylGrignard-Verbindungen mit Arylchloriden,-tosylaten und -triflaten", Angew. Chem., vol. 114(4), p. 635-635, (2002).

* cited by examiner

PYRIDIN-4-YL DERIVATIVES

CROSS-REFERENCE TO RELATED APPLICATIONS

This application is a National Stage Entry of International Application No. PCT/IB2014/059794, filed on Mar. 14, 2014, which claims priority from European Patent Application No. 13159482.2, filed on Mar. 15, 2013, the contents of each of which are hereby incorporated by reference in their entirety.

FIELD OF THE INVENTION

The present invention relates to $S1P_1/EDG1$ receptor agonists of Formula (I) and their use as active ingredients in the preparation of pharmaceutical compositions. The invention also concerns related aspects including processes for the preparation of the compounds, pharmaceutical compositions containing a compound of the Formula (I), and their use as compounds improving vascular function and as immunomodulating agents, either alone or in combination with other active compounds or therapies.

DESCRIPTION OF THE INVENTION

The human immune system is designed to defend the body against foreign micro-organisms and substances that cause infection or disease. Complex regulatory mechanisms ensure that the immune response is targeted against the intruding substance or organism and not against the host. In some cases, these control mechanisms are unregulated and autoimmune responses can develop. A consequence of the uncontrolled inflammatory response is severe organ, cell, tissue or joint damage. With current treatment, the whole immune system is usually suppressed and the body's ability to react to infections is also severely compromised. Typical drugs in this class include azathioprine, chlorambucil, cyclophosphamide, cyclosporin, or methotrexate. Corticosteroids which reduce inflammation and suppress the immune response, may cause side effects when used in long term treatment. Nonsteroidal anti-inflammatory drugs (NSAIDs) can reduce pain and inflammation, however, they exhibit considerable side effects. Alternative treatments include agents that activate or block cytokine signaling.

Orally active compounds with immunomodulating properties, without compromising immune responses and with reduced side effects would significantly improve current treatments of uncontrolled inflammatory diseases.

In the field of organ transplantation the host immune response must be suppressed to prevent organ rejection. Organ transplant recipients can experience some rejection even when they are taking immunosuppressive drugs. Rejection occurs most frequently in the first few weeks after transplantation, but rejection episodes can also happen months or even years after transplantation. Combinations of up to three or four medications are commonly used to give maximum protection against rejection while minimizing side effects. Current standard drugs used to treat the rejection of transplanted organs interfere with discrete intracellular pathways in the activation of T-type or B-type white blood cells. Examples of such drugs are cyclosporin, daclizumab, basiliximab, everolimus, or FK506, which interfere with cytokine release or signaling; azathioprine or leflunomide, which inhibit nucleotide synthesis; or 15-deoxyspergualin, an inhibitor of leukocyte differentiation.

The beneficial effects of broad immunosuppressive therapies relate to their effects; however, the generalized immunosuppression which these drugs produce diminishes the immune system's defense against infection and malignancies. Furthermore, standard immunosuppressive drugs are often used at high dosages and can cause or accelerate organ damage.

DETAILED DESCRIPTION OF THE INVENTION

The present invention provides novel compounds of Formula (I) that are agonists for the G protein-coupled receptor $S1P_1/EDG1$ and have a powerful and long-lasting immunomodulating effect which is achieved by reducing the number of circulating and infiltrating T- and B-lymphocytes, without affecting their maturation, memory, or expansion. The reduction of circulating T-/B-lymphocytes as a result of $S1P_1/EDG1$ receptor agonism, possibly in combination with the observed improvement of endothelial cell layer function associated with $S1P_1/EDG1$ receptor activation, makes such compounds useful to treat uncontrolled inflammatory diseases and to improve vascular functionality. Prior art document WO 2008/029371 (document D1) discloses compounds that act as $S1P_1/EDG1$ receptor agonists and show an immunomodulating effect as described above. On the other hand, several reports suggest that activation of the $S1P_3$ receptor is associated with vaso- and bronchoconstriction (e.g. Salomone et al. *Brit. J. Pharmacol.* 153 (2008) 140-147; Murakami et al. *Mol. Pharmacol.* 77 (2010) 704-713; Lucke et al. *Cellular Physiology and Biochemistry* 26 (2010) 87-96), blood pressure increase (e.g. Fryer et al. *PLOS One* 7 (2012) e52985), heart rate reduction (e.g. Hamada et. al. *J. Med. Chem.* 53 (2010) 3154-3168) and pulmonary epithelial leakage (e.g. Gon et al. *PNAS* 102 (2005) 9270-9275). Selectivity against the $S1P_3$ receptor is therefore deemed an advantage of a given $S1P_1$ receptor agonist (e.g. Hale et al. *Bioorg. Med. Chem. Lett.* 14 (2004) 3501-3505).

Unexpectedly, it has been found that the compounds of the present invention have a reduced activity on the $S1P_3$ receptor when compared to closest analogs disclosed in document D1. This becomes evident from the data listed in Table 1 and Table 2. The compound of Example 1 of the present invention, for instance, shows an $EC_{50}$ of 9950 nM for the $S1P_3$ receptor while its closest analog in document D1 (Example 57 of D1) shows an $EC_{50}$ value of 1540 nM. Similarly, the compound of Example 2 is clearly less potent on $S1P_3$ receptor when compared to its closest analog disclosed in document D1 (Example 101 of D1). Also, Example 5 of the present invention is significantly less potent on $S1P_3$ receptor when compared to its analog of document D1 (S-enantiomer of the racemate of Example 22 of D1), and the same is true for the compounds of Examples 7 and 8 and their corresponding analogs in document D1 (Example 204 and Example 233, respectively, of D1).

TABLE 1

![structure]

| Example | R¹ | EC$_{50}$ [nM] S1P$_1$ | EC$_{50}$ [nM] S1P$_3$ |
|---|---|---|---|
| 1 | ethyl | 2.1 | 9950 |
| 2 | n-propyl | 0.7 | 1120 |
| 3 | isopropyl | 0.3 | 3940 |
| 4 | n-butyl | 1.8 | 700 |
| 5 | isobutyl | 0.2 | 757 |
| 6 | isopentyl | 5.1 | 2600 |
| 7 | pent-3-yl | 0.1 | 1340 |
| 8 | cyclopentyl | 0.1 | 736 |

TABLE 2

| Closest Analog in D1 | R¹ | EC$_{50}$ [nM] S1P$_1$ | EC$_{50}$ [nM] S1P$_3$ |
|---|---|---|---|
| to Example 1 (Example 57 of D1) | ethyl | 0.3 | 1540 |
| to Example 2 (Example 101 of D1) | n-propyl | 0.4 | 310 |
| to Example 5 (S-entiomer of Example 22 of D1) | isobutyl | 0.1 | 33 |
| to Example 7 (Example 204 of D1) | pent-3-yl | 0.2 | 44 |
| to Example 8 (Example 233 of D1) | cyclopentyl | 0.2 | 47 |

Taken together, the data presented in Table 1 and 2 clearly demonstrate that with respect to reduced activity on the S1P$_3$ receptor, the pyridine derivatives of the present invention are superior to the corresponding 2-methyl-pyridine analogs disclosed in document D1, regardless of the nature of substituent R¹ of the compounds of Formula (I) of the present invention.

The compounds of the present invention can be utilized alone or in combination with standard drugs inhibiting T-cell activation, to provide a new immunomodulating therapy with a reduced propensity for infections when compared to standard immunosuppressive therapy. Furthermore, the compounds of the present invention can be used in combination with reduced dosages of traditional immunosuppressant therapies, to provide on the one hand effective immunomodulating activity, while on the other hand reducing end organ damage associated with higher doses of standard immunosuppressive drugs. The observation of improved endothelial cell layer function associated with S1P$_1$/EDG1 receptor activation provides additional benefits of compounds to improve vascular function.

The nucleotide sequence and the amino acid sequence for the human S1P$_1$/EDG1 and S1P$_3$/EDG3 receptors are known in the art and are published in e.g.: Hla, T., and Maciag, T., *J. Biol Chem.* 265 (1990), 9308-9313; WO 91/15583 published 17 Oct. 1991; WO 99/46277 published 16 Sep. 1999; Yamaguchi F., Tokuda M., Hatase O., Brenner S., *Biochem. Biophys. Res. Commun.* 227 (1996), 608-614; An S., Bleu T., Huang W., Hallmark O. G., Coughlin S. R., Goetzl E. J., *FEBS Lett.* 417 (1997), 279-282. The potency and efficacy of the compounds of Formula (I) are assessed using a GTPγS assay to determine EC$_{50}$ values and by measuring the circulating lymphocytes in the rat after oral administration, respectively (see in experimental part).

i) In a first embodiment, the invention relates to a compound of the Formula (I),

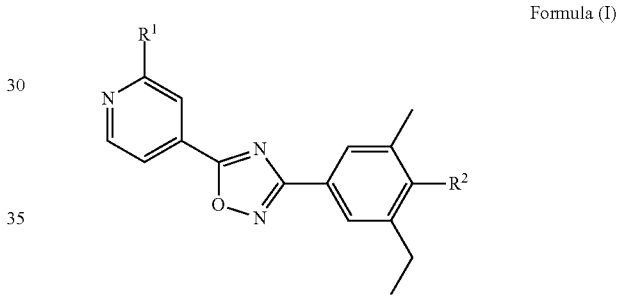

Formula (I)

wherein
R¹ represents C$_{2-5}$-alkyl, preferably wherein the carbon atom which is attached to the pyridine ring carries at least one hydrogen atom, or cyclopentyl; and
R² represents —OCH$_2$—CH(OH)—CH$_2$—NHCO—CH$_2$OH.

ii) Another embodiment of the invention relates to a compound according to embodiment i), wherein R¹ represents ethyl, n-propyl, isopropyl, n-butyl, isobutyl, isopentyl, pent-3-yl, or cyclopentyl.

iii) Another embodiment of the invention relates to a compound according to embodiment i), wherein R¹ represents n-propyl, isopropyl, isobutyl, or cyclopentyl.

iv) Another embodiment of the invention relates a compound according to embodiment i), wherein R¹ represents cyclopentyl.

v) Another embodiment of the invention relates to a compound according to any one of embodiments i) to iv), wherein the stereocenter of the R² group —OCH$_2$—CH(OH)—CH$_2$—NHCO—CH$_2$OH is in the S-configuration.

The term C$_{2-5}$-alkyl means saturated, branched or straight chain alkyl groups with two to five carbon atoms.

The compounds of Formula (I) may contain one or more stereogenic or asymmetric centers, such as one or more asymmetric carbon atoms. The compounds of Formula (I) may thus be present as mixtures of stereoisomers or preferably as pure stereoisomers. Mixtures of stereoisomers may be separated in a manner known to a person skilled in the art.

Where the plural form is used for compounds, salts, pharmaceutical compositions, diseases and the like, this is intended to mean also a single compound, salt, or the like.

Any reference hereinbefore or hereinafter to a compound of Formula (I) is to be understood as referring also to salts, especially pharmaceutically acceptable salts, of a compound of Formula (I), as appropriate and expedient.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example 'Handbook of Pharmaceutical Salts. Properties, Selection and Use.', P. Heinrich Stahl, Camille G. Wermuth (Eds.), Wiley-VCH, 2008 and 'Pharmaceutical Salts and Co-crystals', Johan Wouters and Luc Quéré (Eds.), RSC Publishing, 2012.

The present invention also includes isotopically labelled, especially $^2$H (deuterium) labelled compounds of Formula (I), which compounds are identical to the compounds of Formula (I) except that one or more atoms have each been replaced by an atom having the same atomic number but an atomic mass different from the atomic mass usually found in nature. Isotopically labelled, especially $^2$H (deuterium) labelled compounds of Formula (I) and salts thereof are within the scope of the present invention. Substitution of hydrogen with the heavier isotope $^2$H (deuterium) may lead to greater metabolic stability, resulting e.g. in increased in vivo half-life or reduced dosage requirements, or may lead to reduced inhibition of cytochrome P450 enzymes, resulting e.g. in an improved safety profile. In one embodiment of the invention, the compounds of Formula (I) are not isotopically labelled, or they are labelled only with one or more deuterium atoms. In a sub-embodiment, the compounds of Formula (I) are not isotopically labelled at all. Isotopically labelled compounds of Formula (I) may be prepared in analogy to the methods described hereinafter, but using the appropriate isotopic variation of suitable reagents or starting materials.

Examples of pyridine compounds according to Formula (I) are selected from:
- (S)—N-(3-(2-ethyl-4-(5-(2-ethylpyridin-4-yl)-1,2,4-oxadiazol-3-yl)-6-methyl-phenoxy)-2-hydroxypropyl)-2-hydroxyacetamide;
- (S)—N-(3-(2-ethyl-4-(5-(2-propylpyridin-4-yl)-1,2,4-oxadiazol-3-yl)-6-methyl-phenoxy)-2-hydroxypropyl)-2-hydroxyacetamide;
- (S)—N-(3-(2-ethyl-4-(5-(2-isopropylpyridin-4-yl)-1,2,4-oxadiazol-3-yl)-6-methylphenoxy)-2-hydroxypropyl)-2-hydroxyacetamide;
- (S)—N-(3-(2-ethyl-4-(5-(2-butylpyridin-4-yl)-1,2,4-oxadiazol-3-yl)-6-methylphenoxy)-2-hydroxypropyl)-2-hydroxyacetamide;
- (S)—N-(3-(2-ethyl-4-(5-(2-isobutylpyridin-4-yl)-1,2,4-oxadiazol-3-yl)-6-methylphenoxy)-2-hydroxypropyl)-2-hydroxyacetamide;
- (S)—N-(3-(2-ethyl-4-(5-(2-isopentylpyridin-4-yl)-1,2,4-oxadiazol-3-yl)-6-methylphenoxy)-2-hydroxypropyl)-2-hydroxyacetamide;
- (S)—N-(3-(2-ethyl-4-(5-(2-(pentan-3-yl)-pyridin-4-yl)-1,2,4-oxadiazol-3-yl)-6-methylphenoxy)-2-hydroxypropyl)-2-hydroxyacetamide; and
- (S)—N-(3-(2-ethyl-4-(5-(2-cyclopentylpyridin-4-yl)-1,2,4-oxadiazol-3-yl)-6-methylphenoxy)-2-hydroxypropyl)-2-hydroxyacetamide.

The compounds of Formula (I) and their pharmaceutically acceptable salts can be used as medicaments, e.g. in the form of pharmaceutical compositions for enteral (such as especially oral) or parenteral (including topical application or inhalation) administration, and are suitable for decreasing the number of circulating lymphocytes and for the prevention and/or treatment of diseases or disorders associated with an activated immune system.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of Formula (I) or their pharmaceutically acceptable salts, optionally in combination with other therapeutically valuable substances, into a galenical administration form together with suitable, non-toxic, inert, pharmaceutically acceptable solid or liquid carrier materials and, if desired, usual pharmaceutical adjuvants.

The pharmaceutical compositions comprising a compound of Formula (I) are useful for the prevention and/or treatment of diseases or disorders associated with an activated immune system.

Such diseases or disorders associated with an activated immune system and to be prevented/treated with the compounds of Formula (I) are for example selected from the group consisting of rejection of transplanted organs, tissue or cells; graft-versus-host diseases brought about by transplantation; autoimmune syndromes including rheumatoid arthritis; systemic lupus erythematosus; antiphospholipid syndrome; Hashimoto's thyroiditis; lymphocytic thyroiditis; multiple sclerosis; myasthenia gravis; type I diabetes; uveitis; episcleritis; scleritis; Kawasaki's disease, uveoretinitis; posterior uveitis; uveitis associated with Behcet's disease; uveomeningitis syndrome; allergic encephalomyelitis; chronic allograft vasculopathy; post-infectious autoimmune diseases including rheumatic fever and post-infectious glomerulonephritis; inflammatory and hyperproliferative skin diseases; psoriasis; psoriatic arthritis; atopic dermatitis; myopathy; myositis; osteomyelitis; contact dermatitis; eczematous dermatitis; seborrhoeic dermatitis; lichen planus; pemphigus; bullous pemphigoid; epidermolysis bullosa; urticaria; angioedema; vasculitis; erythema; cutaneous eosinophilia; acne; scleroderma; alopecia areata; keratoconjunctivitis; vernal conjunctivitis; keratitis; herpetic keratitis; dystrophia epithelialis corneae; corneal leukoma; ocular pemphigus; Mooren's ulcer; ulcerative keratitis; scleritis; Graves' ophthalmopathy; Vogt-Koyanagi-Harada syndrome; sarcoidosis; pollen allergies; reversible obstructive airway disease; bronchial asthma; allergic asthma; intrinsic asthma; extrinsic asthma; dust asthma; chronic or inveterate asthma; late asthma and airway hyper-responsiveness; bronchiolitis; bronchitis; endometriosis; orchitis; gastric ulcers; ischemic bowel diseases; inflammatory bowel diseases; necrotizing enterocolitis; intestinal lesions associated with thermal burns; coeliac disease; proctitis; eosinophilic gastroenteritis; mastocytosis; Crohn's disease; ulcerative colitis; vascular damage caused by ischemic diseases and thrombosis; atherosclerosis; fatty heart; myocarditis; cardiac infarction; aortitis syndrome; cachexia due to viral disease; vascular thrombosis; migraine; rhinitis; eczema; interstitial nephritis; IgA-induced nephropathy; Goodpasture's syndrome; hemolytic-uremic syndrome; diabetic nephropathy; glomerulosclerosis; glomerulonephritis; tubulointerstitial nephritis; interstitial cystitis; multiple myositis; Guillain-Barré syndrome; Meniere's disease; polyneuritis; multiple neuritis; myelitis; mononeuritis; radiculopathy; hyperthyroidism; Basedow's disease; thyrotoxicosis; pure red cell aplasia; aplastic anemia; hypoplastic anemia; idiopathic thrombocytopenic purpura; autoimmune hemolytic anemia; autoimmune thrombocytopenia; agranulocytosis; pernicious anemia; megaloblastic anemia; anerythroplasia; osteoporosis; fibroid lung; idiopathic interstitial pneumonia; dermatomyositis; leukoderma vulgaris; ichthyosis vulgaris; photoallergic sensitivity; cutaneous T cell lymphoma; polyarteritis nodosa; Huntington's chorea; Sydenham's chorea; myocardosis; myocarditis; scleroderma; Wegener's granuloma; Sjogren's syndrome; adiposis; eosinophilic fasciitis; lesions of gingiva, periodontium, alveolar bone, substantia ossea dentis; male pattern alopecia or alopecia senilis; muscular dystrophy; pyoderma; Sezary's syndrome; hypophysitis; chronic adrenal insufficiency; Addison's disease; ischemia-reperfusion injury of organs which occurs upon preservation; endotoxin shock; pseudomembranous colitis; colitis caused by drug or radiation; ischemic acute renal insufficiency; chronic renal insufficiency; lung cancer; malignancy of lymphoid origin; acute or chronic lymphocytic leukemias; lymphoma; pulmonary emphysema; cataracta; siderosis; retinitis pigmentosa; senile macular degeneration; vitreal scarring; corneal alkali burn; dermatitis erythema; ballous dermatitis; cement dermatitis; gingivitis; periodontitis; sepsis; pancreatitis; peripheral artery disease; carcinogenesis; solid cancer tumors; metastasis of carcinoma; hypobaropathy; autoimmune hepatitis; primary biliary cirrhosis; sclerosing cholangitis; partial liver resection; acute liver necrosis; cirrhosis; alcoholic cirrhosis; hepatic failure; fulminant hepatic failure; late-onset hepatic failure; and "acute-on-chronic" liver failure.

Preferred diseases or disorders to be treated and/or prevented with the compounds of Formula (I) are selected from the group consisting of rejection of transplanted organs such as kidney, liver, heart, lung, pancreas, cornea, and skin; graft-versus-host diseases brought about by stem cell transplantation; autoimmune syndromes including rheumatoid arthritis, multiple sclerosis, inflammatory bowel diseases such as Crohn's disease and ulcerative colitis, psoriasis, psoriatic arthritis, thyroiditis such as Hashimoto's thyroiditis, and uveo-retinitis; atopic diseases such as rhinitis, conjunctivitis, and atopic dermatitis; asthma; type I diabetes; post-infectious autoimmune diseases including rheumatic fever and post-infectious glomerulonephritis; and solid cancers and tumor metastasis.

Particularly preferred diseases or disorders to be treated and/or prevented with the compounds of Formula (I) are selected from the group consisting of rejection of transplanted organs selected from kidney, liver, heart and lung; graft-versus-host diseases brought about by stem cell transplantation; autoimmune syndromes selected from rheumatoid arthritis, multiple sclerosis, psoriasis, psoriatic arthritis, Crohn's disease, and Hashimoto's thyroiditis; and atopic dermatitis. Very preferably the diseases or disorders to be treated and/or prevented with the compounds of Formula (I) are selected from multiple sclerosis and psoriasis.

The present invention also relates to a method for the prevention or treatment of a disease or disorder mentioned herein comprising administering to a subject a pharmaceutically active amount of a compound of Formula (I).

Furthermore, compounds of the Formula (I) are also useful, in combination with one or several immunomodulating agents, for the prevention and/or treatment of the diseases and disorders mentioned herein. According to a preferred embodiment of the invention, said agents are selected from the group consisting of immunosuppressants, corticosteroids, NSAID's, cytotoxic drugs, adhesion molecule inhibitors, cytokines, cytokine inhibitors, cytokine receptor antagonists and recombinant cytokine receptors.

The present invention also relates to the use of a compound of Formula (I) for the preparation of a pharmaceutical composition, optionally for use in combination with one or several immunomodulating agents, for the prevention or treatment of the diseases and disorders mentioned herein.

The compounds of Formula (I) can be manufactured by the methods given below, by the methods given in the Examples or by analogous methods. Optimum reaction conditions may vary with the particular reactants or solvents used, but such conditions can be determined by a person skilled in the art by routine optimisation procedures.

Compounds of the Formula (I) of the present invention can be prepared according to the general sequence of reactions outlined below. Only a few of the synthetic possibilities leading to compounds of Formula (I) are described.

Compounds of Formula (I) are prepared by reacting a compound of Structure 1 in a solvent such as toluene, pyridine, DMF, THF, dioxane, DME, etc. at rt or elevated temperatures in the presence or absence of auxiliaries such as acids (e.g. TFA, acetic acid, HCl, etc.), bases (e.g. NaH, NaOAc, $Na_2CO_3$, $K_2CO_3$, $NEt_3$, etc.), tetraalkylammonium salts, or water removing agents (e.g. oxalyl chloride, a carboxylic acid anhydride, $POCl_3$, $PCl_5$, $P_4O_{10}$, molecular sieves, Burgess reagent, etc.) (Lit.: e.g. A. R. Gangloff, J. Litvak, E. J. Shelton, D. Sperandio, V. R. Wang, K. D. Rice, *Tetrahedron Lett.* 42 (2001), 1441-1443; T. Suzuki, K. Iwaoka, N. Imanishi, Y. Nagakura, K. Miyta, H. Nakahara, M. Ohta, T. Mase, *Chem. Pharm. Bull.* 47 (1999), 120-122; R. F. Poulain, A. L. Tartar, B. P. Déprez, *Tetrahedron Lett.* 42 (2001), 1495-1498; R. M. Srivastava, F. J. S. Oliveira, D. S. Machado, R. M. Souto-Maior, *Synthetic Commun.* 29 (1999), 1437-1450; E. O. John, J. M. Shreeve, *Inorganic Chemistry* 27 (1988), 3100-3104; B. Kaboudin, K. Navaee, *Heterocycles* 60 (2003), 2287-2292).

Structure 1

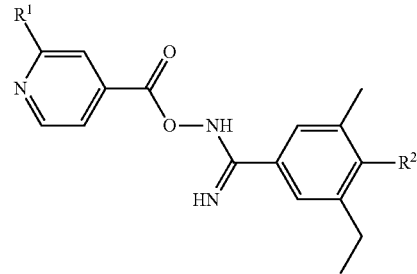

Compounds of Structure 1 may be prepared by reacting a compound of Structure 2 with a compound of Structure 3 in a solvent such as DMF, THF, DCM, etc. in the presence of one or more coupling agents such as TBTU, DCC, EDC, HBTU, CDI, etc. and in the presence or absence of a base such as $NEt_3$, DIPEA, NaH, $K_2CO_3$, etc. (Lit.: e.g. A. Hamze, J.-F. Hernandez, P. Fulcrand, J. Martinez, *J. Org. Chem.* 68 (2003), 7316-7321; and the literature cited above).

Structure 2

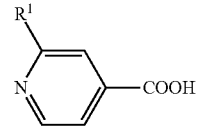

Structure 3

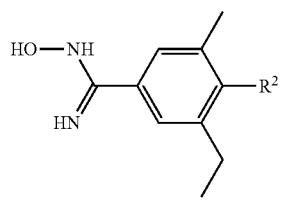

Compounds of Structure 3 may be prepared by reacting a compound of Structure 4, with hydroxylamine or one of its salts in a solvent such as MeOH, EtOH, pyridine, etc. in the presence or absence of a base such as $Na_2CO_3$, $K_2CO_3$, potassium tert.butylate, $NEt_3$, etc. (Lit.: e.g. E. Meyer, A. C. Joussef, H. Gallardo, *Synthesis* 2003, 899-905, WO 2004/035538 (Merck & Co., Inc., USA)).

Structure 4

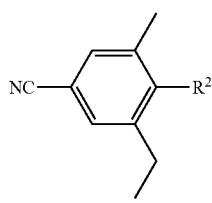

Structure 5

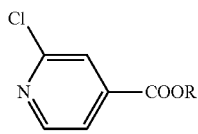

Compounds of Structure 2 may be prepared by reacting 2-chloro-isonicotinic acid or a suitable ester derivative thereof (Structure 5, wherein R represents e.g. methyl, ethyl, isopropyl, etc.) with dialkyl-Zn, an alkyl-Zn or cycloalkyl-Zn halogen reagent under Negishi conditions (Lit.: e.g. H. Matsushita, E. Negishi, *J. Org. Chem.* 47 (1982), 4161-4165), with an appropriate alkyl or cycloalkyl Grignard reagent for instance in the presence of $Fe(acac)_3$ in a solvent such as THF, dioxane, DMF, NMP, etc., or combinations thereof, at temperatures ranging from –78 to 25° C. under Fürstner conditions (Lit.: e.g. A. Fürstner, A. Leitner, M. Mendez, H. Krause, *J. Am. Chem. Soc.* 124 (2002), 13856-13863; A. Fürstner, A. Leitner, *Angew. Chem.* 114 (2002), 632-635) or with 1-alkenyl or cycloalken-1-yl-boron derivative (Lit.: e.g. F. Kerins, D. F. O'Shea, *J. Org. Chem.* 67 (2002), 4968-4971) under Suzuki coupling conditions (Lit.: e.g. H. Doucet, *Eur. J. Org. Chem.* 2008, 2013-2030). In case 1-alkenyl boron derivatives are used to introduce the carbon framework of $R^1$, a subsequent hydrogenation step is required to establish the desired alkyl or cycloalkyl group. Finally, in case a pyridine-4-carboxylic acid ester has been employed in the steps described above, ester hydrolysis under basic or acid reaction conditions furnishes the desired compound of Structure 2.

Whenever the compounds of Formula (I) are obtained in the form of mixtures of stereoisomers such as especially enantiomers, the stereoisomers can be separated using methods known to one skilled in the art: e.g. by formation and separation of diastereomeric salts or by HPLC over a chiral stationary phase such as a Daicel ChiralPak AD-H (5 µm) column, a Daicel ChiralCel OD-H (5 µm) column, a Daicel ChiralCel OD (10 µm) column, a Daicel ChiralPak IA (5 µm) column, a Daicel ChiralPak IB (5 µm) column, a Daicel ChiralPak IC (5 µm) column, or a (R,R)-Whelk-01 (5 µm) column. Typical conditions of chiral HPLC are an isocratic mixture of eluent A (EtOH, in presence or absence of a base like $NEt_3$ and/or diethylamine or of an acid like TFA) and eluent B (heptane).

Experimental Part

The following examples illustrate the invention but do not at all limit the scope thereof.

All temperatures are stated in ° C. Compounds are characterized by $^1$H-NMR (300 MHz) or $^{13}$C-NMR (75 MHz) (Varian Oxford; chemical shifts are given in ppm relative to the solvent used; multiplicities: s=singlet, d=doublet, t=triplet, p=pentuplet, hex=hexet, hept=heptet, m=multiplet, br=broad, coupling constants are given in Hz); by LC-MS (Finnigan Navigator with HP 1100 Binary Pump and DAD, column: 4.6×50 mm, Zorbax SB-AQ, 5 µm, 120 Å, gradient: 5-95% MeCN in water, 1 min, with 0.04% TFA, flow: 4.5 mL/min, $t_R$ is given in min; by TLC (TLC-plates from Merck, Silica gel 60 $F_{254}$); or by melting point. Compounds are purified by prep. HPLC (column: X-terra RP18, 50×19 mm, 5 µm, gradient: 10-95% MeCN in water containing 0.5% of formic acid) or by MPLC (Labomatic MD-80-100 pump, Linear UVIS-201 detector, column: 350×18 mm, Labogel-RP-18-5s-100, gradient: 10% MeOH in water to 100% MeOH).

ABBREVIATIONS

As Used Herein aq. aqueous
BSA bovine serum albumin
Burgess reagent methoxycarbonylsulfamoyl triethylammonium hydroxide
CC column chromatography
CDI carbonyl diimidazole
DCC N,N'-dicyclohexyl carbodiimide
DCM dichloromethane
DEAD diethyl-diazodicarboxylate
DIPEA Hüning's base, diethylisopropylamine
DME 1,2-dimethoxyethane
DMF dimethylformamide
DMSO dimethylsulfoxide
dppf 1,1'-bis(diphenylphosphino)ferrocene
EA ethyl acetate
EDC N-(3-dimethylaminopropyl)-N'-ethyl-carbodiimide
Et ethyl
EtOH ethanol
$Fe(acac)_3$ iron(III) acetylacetone-complex
h hour(s)
HBTU O-(benzotriazol-1-yl)-N,N,N',N'-tetramethyluronium hexafluorophosphate
HEPES 4-(2-hydroxyethyl)-1-piperazineethanesulfonic acid
HOBt 1-hydroxy-benzotriazole
HPLC high performance liquid chromatography
LC-HRMS liquid chromatography—high resolution mass spectrometry
LC-MS liquid chromatography—mass spectrometry
Lit. literature
Me methyl
MeCN acetonitrile
MeOH methanol
min minute(s)
MPLC medium pressure liquid chromatography
NaOAc sodium acetate NEt₃ triethylamine
NMP 1-methyl-2-pyrrolidone
org. organic
PPh₃ triphenylphosphine
prep. preparative
quant. quantitative
rt room temperature
sat. saturated
S1P sphingosine 1-phosphate
TBTU 2-(1H-benzotriazole-1-yl)-1,2,3,3-tetramethyluronium tetrafluoroborate
tert. tertiary
TFA trifluoroacetic acid
THF tetrahydrofuran
TLC thin layer chromatography
$t_R$ retention time Preparation of Intermediates N—((S)-3-[2-Ethyl-4-(N-hydroxycarbamimidoyl)-6-methyl-phenoxy]-2-hydroxy-propyl)-2-hydroxy-acetamide a) To an ice-cold solution of H₂SO₄ (150 mL) in water (250 mL), 2-ethyl-6-methylaniline (15.0 g, 111 mmol) is added. The solution is treated with ice (150 g) before a solution of NaNO₂ (10.7 g, 155 mmol) in water (150 mL) and ice (50 g) is added dropwise. The mixture is stirred at 0° C. for 1 h. 50% aq. H₂SO₄ (200 mL) is added and stirring is continued at rt for 18 h. The mixture is extracted with DCM, the org. extracts are dried over MgSO₄ and evaporated. The crude product is purified by CC on silica gel eluting with heptane:EA 9:1 to give 2-ethyl-6-methyl-phenol (8.6 g, 57%) as a crimson oil; LC-MS: $t_R$=0.89 min; ¹H NMR (CDCl₃): δ 7.03-6.95 (m, 2H), 6.80 (t, J=7.6 Hz, 1H), 4.60 (s, 1H), 2.64 (q, J=7.6 Hz, 2H), 2.25 (s, 3H), 1.24 (t, J=7.6 Hz, 3H).

b) A solution of 2-ethyl-6-methyl phenol (200 g, 1.47 mol) and hexamethylene tetraamine (206 g, 1.47 mol) in acetic acid (1600 mL) and water (264 mL) is heated to reflux. The condensate is removed using a Dean-Stark apparatus until about 1200 mL of condensate are collected. The reaction mixture is cooled to rt and water (1000 mL) is added. The thick suspension is filtered and the collected solid is dried at 60° C. under vacuum (10 mbar) to give 3-ethyl-4-hydroxy-5-methyl-benzaldehyde (191 g, 79%) as an orange solid; LC-MS: $t_R$=0.86 min, [M+1+CH₃CN]⁺=206.27; ¹H NMR (CDCl₃): δ 9.84 (s, 1 H), 7.59 (s, 1 H), 7.57 (s, 1 H), 4.64 (s br, 1 H), 2.71 (q, J=7.5 Hz, 2 H), 2.34 (s, 3 H), 1.30 (t, J=7.5 Hz, 3 H).

c) A solution of 3-ethyl-4-hydroxy-5-methyl-benzaldehyde (5.32 g, 32.4 mmol) and hydroxylamine hydrochloride (3.38 g, 48.6 mmol) in NMP (35 mL) is stirred for 3 h at 80° C. under microwave irradiation (300 W, continuous cooling, A. K. Chakraborti, G. Kaur, Tetrahedron 55 (1999) 13265-13268). The mixture is diluted with water and extracted twice with diethyl ether. The org. extracts are washed with 2 N aq. HCl, sat. aq. NaHCO₃ solution and brine. The org. extracts are combined, dried over Na₂SO₄, filtered and concentrated. The crude product is purified by CC on silica gel eluting with heptane:EA 3:2 to give 3-ethyl-4-hydroxy-5-methyl-benzonitrile as a pale yellow solid (4.80 g, 92%); LC-MS: $t_R$=0.90 min; ¹H NMR (CDCl₃): δ 1.24 (t, J=7.6 Hz, 3 H), 2.26 (s, 3 H), 2.63 (q, J=7.6 Hz, 2 H), 5.19 (s, 1 H), 7.30 (s, 2 H).

d) To a solution of 3-ethyl-4-hydroxy-5-methyl-benzonitrile (5.06 g, 31.4 mmol) in THF (80 mL), PPh₃ (9.06 g, 34.5 mmol) and (R)-glycidol (2.29 mL, 34.5 mmol) are added. The mixture is cooled to 0° C. before DEAD in toluene (15.8 mL, 34.5 mmol) is added. The mixture is stirred for 18 h while warming up to rt. The solvent is evaporated and the crude product is purified by CC on silica gel eluting with heptane:EA 7:3 to give (S)-3-ethyl-5-methyl-4-(oxiran-2-ylmethoxy)benzonitrile (5.85 g, 86%) as a yellow oil; LC-MS: $t_R$=0.96 min, [M+42]⁺=259.08; ¹H NMR (CDCl₃): δ 7.38 (s, 1 H), 7.35 (s, 1 H), 4.12-4.19 (m, 1 H), 3.73-3.80 (m, 1 H), 3.36-3.42 (m, 1 H), 2.90-2.96 (m, 1 H), 2.68-2.77 (m, 3 H), 2.34 (s, 3 H), 1.26 (t, J=7.6 Hz, 3 H).

e) The above (S)-3-ethyl-5-methyl-4-(oxiran-2-ylmethoxy)benzonitrile (5.85 g, 26.9 mmol) is dissolved in 7 N NH₃ in methanol (250 mL) and the solution is stirred at 65° C. for 18 h. The solvent is evaporated to give crude (S)-4-(3-amino-2-hydroxypropoxy)-3-ethyl-5-methylbenzonitrile (6.23 g, quant.) as a yellow oil; LC-MS: $t_R$=0.66 min, [M+1]⁺=235.11; ¹H NMR (D₆-DMSO): δ 7.54 (s, 2 H), 4.96 (s br, 1 H), 3.77-3.83 (m, 1 H), 3.68-3.77 (m, 2 H), 2.59-2.75 (m, 4 H), 2.28 (s, 3 H), 1.58 (s br, 2 H), 1.17 (t, J=7.5 Hz, 3 H).

f) To a solution (S)-4-(3-amino-2-hydroxypropoxy)-3-ethyl-5-methylbenzonitrile (6.23 g, 26.6 mmol), glycolic acid (2.43 g, 31.9 mmol), HOBt (4.31 g, 31.9 mmol), and EDC hydrochloride (6.12 g, 31.9 mmol) are added. The mixture is stirred at it for 18 h before it is diluted with sat. aq. NaHCO₃ and extracted twice with EA. The combined org. extracts are dried over MgSO₄, filtered and concentrated. The crude product is purified by CC with DCM containing 8% of methanol to give (S)—N-[3-(4-cyano-2-ethyl-6-methyl-phenoxy)-2-hydroxy-propyl]-2-hydroxy-acetamide (7.03 g, 90%) as a yellow oil; LC-MS: $t_R$=0.74 min, [M+1]⁺=293.10; ¹H NMR (CDCl₃): δ 1.25 (t, J=7.5 Hz, 3 H), 2.32 (s, 3 H), 2.69 (q, J=7.5 Hz, 2 H), 3.48-3.56 (m, 3 H), 3.70-3.90 (m, 3 H), 4.19 (s, br, 3 H), 7.06 (m, 1 H), 7.36 (s, 1 H), 7.38 (s, 1 H).

g) To a solution of (S)—N-[3-(4-cyano-2-ethyl-6-methyl-phenoxy)-2-hydroxy-propyl]-2-hydroxy-acetamide (19.6 g, 67 mmol) in methanol (500 mL) is added hydroxylamine hydrochloride (9.32 g, 134 mmol) and NaHCO₃ (11.3 g, 134 mmol). The resulting suspension is stirred at 65° C. for 18 h. The mixture is filtered and the filtrate is concentrated. The residue is dissolved in water (20 mL) and EA (300 mL). The aq. phase is separated and extracted three times with EA. The combined org. extracts are dried over MgSO₄, filtered, concentrated and dried to give the title compound as white solid (18.9 g, 87%); LC-MS: $t_R$=0.51 min, [M+1]⁺=326.13; ¹H NMR (D₆-DMSO): δ 1.17 (t, J 7.4 Hz, 3 H), 2.24 (s, 3H), 2.62 (q, J 7.4 Hz, 2 H), 3.23 (m, 1 H), 3.43 (m, 1 H), 3.67 (m, 2 H), 3.83 (s, 2 H), 3.93 (m, 1 H), 5.27 (s br, 1 H), 5.58 (s br, 1 H), 5.70 (s, 2 H), 7.34 (s, 1 H), 7.36 (s, 1 H), 7.67 (m, 1 H), 9.46 (s br, 1H).

2-Ethylisonicotinic Acid

The title compound is prepared as hydrochloride salt in analogy to 2-(pentan-3-yl)isonicotinic acid; LC-MS: $t_R$=0.22 min, [M+1]⁺=152.13; ¹H NMR (CD₃OD): δ 8.68 (d, J=5.4 Hz, 1 H), 7.99 (s, 1 H), 7.91 (dd, J₁=5.3 Hz, J₂=1.3 Hz, 1 H), 2.98 (q, J=7.6 Hz, 2 H), 1.37 (t, J=7.6 Hz, 3 H).

2-Propylisonicotinic Acid

The title compound is prepared as hydrochloride salt in analogy to 2-(pentan-3-yl)isonicotinic acid; LC-MS: $t_R$=0.20 min, [M+1]⁺=166.10. Methyl 2-propylisonicotinate: LC-MS: $t_R$=0.43 min, [M+1]⁺=180.33; ¹H NMR (CDCl₃): δ

8.67 (d, J=5.0 Hz, 1 H), 7.70 (s, 1 H), 7.64 (dd, J₁=5.1 Hz, J₂=1.5 Hz, 1 H), 3.95 (s, 3 H), 2.82-2.87 (m, 2 H), 1.73-1.84 (m, 2 H), 0.97 (t, J=7.4 Hz, 3 H).

2-Isopropylisonicotinic Acid

The title compound is prepared as hydrochloride salt in analogy to 2-(pentan-3-yl)isonicotinic acid; LC-MS: $t_R$=0.18 min, [M+1]⁺=166.09; ¹H NMR (D₇-DMF): δ 8.49 (d, J=4.9 Hz, 1 H), 7.82 (s, 1 H), 7.74 (dd, J₁=4.9 Hz, J₂=1.1 Hz, 1 H), 2.99-3.08 (m, 1 H), 1.25 (d, J=6.9 Hz, 6 H).

2-Butylisonicotinic Acid

The title compound is prepared as hydrochloride salt in analogy to 2-(pentan-3-yl)isonicotinic acid; LC-MS: $t_R$=0.32 min, [M+1]⁺=180.37; ¹H NMR (D₇-DMF): δ 8.98 (d, J=5.8 Hz, 1 H), 8.38 (s, 1 H), 8.30 (dd, J₁=5.8 Hz, J₂=1.4 Hz, 1 H), 3.28-3.34 (m, 2 H), 1.83-1.93 (m, 2 H), 1.36-1.48 (m, 2 H), 0.95 (t, J=7.3 Hz, 3 H).

2-Isobutylisonicotinic Acid a) To a solution of 2-chloroisonicotinic acid (5.00 g, 31.7 mmol) in toluene is added N,N-dimethylformamide di-tert. butylacetyl (17.9 g, 79.3 mmol). The mixture is stirred at 90° C. for 20 h. The mixture is concentrated, filtered and the filtrate is diluted with EA and washed with water, dried over MgSO₄, filtered and concentrated. The crude product is purified by CC on silica gel eluting heptane:EA 5:1 to give tert. butyl 2-chloroisonicotinate (2.23 g, 33%) as a colourless oil; LC-MS: $t_R$=0.98 min, [M+1+CH₃CN]⁺=255.31.

b) Under argon, to a solution of tert. butyl 2-chloroisonicotinate (2.23 g, 10.4 mmol) in THF (50 mL) is added Fe(acac)₃ (405 mg, 1.15 mmol) followed by NMP (1.45 g, 14.6 mmol). The mixture is cooled to −75° C. before isobutylmagnesium chloride (8 mL of a 2 M solution in THF) is added. The mixture is stirred at −75° C. for 1 h, then at it for 1 h. The reaction is quenched by adding water (100 mL) and the mixture is extracted with EA. The org. extract is dried over MgSO₄, filtered and concentrated. The crude product is purified by CC on silica gel eluting with heptane:EA 4:1 to give tert. butyl 2-isobutylisonicotinate (630 mg, 26%) as a pale yellow oil; LC-MS: $t_R$=0.82 min, [M+1]⁺=236.39.

c) A mixture of tert. butyl 2-isobutylisonicotinate (630 mg, 2.68 mmol) in 25% aq. HCl (10 mL) is stirred at 60° C. for 20 h. The mixture is concentrated and dried under high vacuum to give the title compound (640 mg, quant.) as hydrochloride salt; LC-MS: $t_R$=0.47 min, [M+1]⁺=180.09; ¹H NMR (CD₃OD): δ 8.88 (d, J=5.9 Hz, 1 H), 8.34 (s, 1 H), 8.29 (dd, J₁=5.9 Hz, J₂=1.4 Hz, 1 H), 3.00 (d, J=7.4 Hz, 2 H), 2.14-2.24 (m, 1 H), 1.03 (d, J=6.6 Hz, 6 H).

2-Isopentylisonicotinic Acid

The title compound is prepared in analogy to 2-isobutylisonicotinic acid; tert. butyl 2-isopentylisonicotinate: LC-MS: $t_R$=0.88 min, [M+1]⁺=250.40; ¹H NMR (CDCl₃): δ 8.64 (d, J=5.0 Hz, 1 H), 7.66 (s, 1 H), 7.60 (d, J=5.0 Hz, 1 H), 2.82-2.91 (m, 2 H), 1.57-1.70 (m, 12 H), 0.97 (d, J=5.6 Hz, 6 H). Title compound: LC-MS: $t_R$=0.58 min, [M+1]⁺=194.30.

2-(Pentan-3-yl)Isonicotinic Acid

To a solution of methyl 2-chloroisonicotinate (4.59 g, 26.7 mmol) in dry dioxane (120 mL), Pd(dppf) (2.18 g, 2.67 mmol) is added under argon. To this red-brown suspension 3-pentyl zink (11.6 g, 53.5 mmol, 107 mL of a 0.5 M solution in THF) is added and the mixture is stirred at 100° C. for 18 h. The black solution is cooled to rt, diluted with EA (200 mL) and washed with water (100 mL) and 2 N aq. HCl. The washings are extracted four times with DCM (4×100 mL). The combined org. extracts are dried over MgSO₄, filtered and concentrated. The crude product is purified by MPLC on silica gel eluting with a gradient of EA in heptane to give methyl 2-(pentan-3-yl)isonicotinate (1.15 g, 21%) as brownish oil containing a few percent of methyl 2-(pentan-2-yl)isonicotinate; LC-MS: $t_R$=0.62 min; [M+1]⁺= 208.30. This material is dissolved in THF (30 mL) and 25% aq. HCl (25 mL) and the mixture is stirred at 70° C. for 18 h before it is concentrated and dried to give the title compound (467 mg, 37%) as a beige solid; LC-MS: $t_R$=0.35 min, [M+1]⁺=194.28; ¹H NMR (CD₃OD): δ 8.74 (d, J=5.2 Hz, 1 H), 7.97 (s, 1 H), 7.96 (d, J=6.0 Hz, 1 H), 2.74-2.84 (m, 1 H), 1.71-1.91 (m, 4 H), 0.83 (t, J=7.4 Hz, 6 H).

2-Cyclopentylisonicotinic Acid

The title compound is prepared in analogy to 2-(pentan-3-yl)isonicotinic acid; LC-MS: $t_R$=0.42 min, [M+1]⁺= 192.28; ¹H NMR (CDCl₃): δ 8.93 (s, 1 H), 8.17-8.37 (m, 2 H), 3.77-3.91 (m, 1 H), 2.36-2.48 (m, 2 H), 1.80-1.94 (m, 4 H), 1.70-1.79 (m, 2 H).

EXAMPLES

Example 1

(S)—N-(3-(2-Ethyl-4-(5-(2-ethylpyridin-4-yl)-1,2,4-oxadiazol-3-yl)-6-methyl-phenoxy)-2-hydroxypropyl)-2-hydroxyacetamide

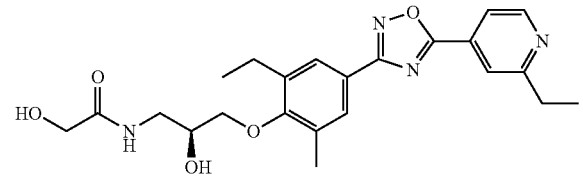 [SMILES: CCc1cc(-c2nc(-c3cc(C)c(OC[C@@H](O)CNC(=O)CO)c(CC)c3)no2)ccn1]

To a solution of N—((S)-3-[2-ethyl-4-(N-hydroxycarbamimidoyl)-6-methyl-phenoxy]-2-hydroxy-propyl)-2-hydroxy-acetamide (290 mg, 1.60 mmol) in DMF (15 mL), EDC HCl (307 mg, 1.60 mmol) and HOBt (216 mg, 1.60 mmol) is added. The mixture is stirred at it for 20 min before 2-ethyl-isonicotinic acid (347 mg, 1.07 mmol) is added. Stirring is continued at it for 1 h. The mixture is diluted with ethyl acetate (50 mL) and washed twice with sat. aq. NaHCO₃ solution (2×10 mL) and brine (1×10 mL). The org. extract is dried over MgSO₄, filtered and concentrated. The remaining residue is dissolved in dioxane (8 mL) and the mixture is stirred at 120° C. for 1 h. The mixture is concentrated and the crude product is purified by prep. HPLC (Waters XBridge 10 μm, 75×30 mm ID, eluting with a gradient of acetonitrile in water containing 0.5% of formic acid) to give the title compound (114 mg) as pale beige solid; LC-MS: $t_R$=0.63 min, [M+1]⁺=441.23; ¹H NMR (CDCl₃): δ 8.77 (d, J=5.0 Hz, 1 H), 7.94 (s, 1 H), 7.84-7.88 (m, 3 H), 7.20 (t, J=5.5 Hz, 1 H), 4.18-4.25 (m, 3 H), 3.90 (dd, J₁=9.5 Hz, J₂=4.5 Hz, 1 H), 3.85 (dd, J₁=9.5 Hz, J₂=6.3 Hz, 1 H), 3.79 (ddd, J₁=14.1 Hz, J₂=6.5 Hz, J₃=3.3 Hz, 1 H), 3.72 (s br, 1 H), 3.49-3.58 (m, 1 H), 2.99 (q, J=7.6 Hz, 2 H), 2.75 (q, J=7.5 Hz, 2 H), 2.38 (s, 3 H), 1.41 (t, J=7.6 Hz, 3 H), 1.32 (t, J=7.5 Hz, 3 H).

Example 2

(S)—N-(3-(2-ethyl-4-(5-(2-propylpyridin-4-yl)-1,2,4-oxadiazol-3-yl)-6-methyl-phenoxy)-2-hydroxypropyl)-2-hydroxyacetamide

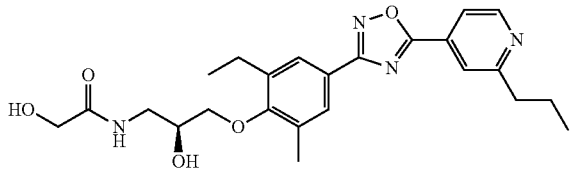 [SMILES: CCCc1cc(-c2nc(-c3cc(C)c(OC[C@@H](O)CNC(=O)CO)c(CC)c3)no2)ccn1]

Prepared in analogy to Example 1. Beige solid; LC-MS: $t_R$=0.68 min, [M+1]$^+$=455.22; $^1$H NMR (CDCl$_3$): δ 8.77 (d, J=5.1 Hz, 1 H), 7.93 (s, 1 H), 7.84-7.89 (m, 3 H), 7.20 (t br, J=5.8 Hz, 1 H), 4.18-4.25 (m, 3 H), 3.90 (dd, $J_1$=9.6 Hz, $J_2$=4.7 Hz, 1 H), 3.85 (dd, =9.5 Hz, $J_2$=6.1 Hz, 1 H), 3.79 (ddd, $J_1$=14.1 Hz, $J_2$=6.5 Hz, $J_3$=3.0 Hz, 1 H), 3.49-3.58 (m, 1 H), 2.90-2.96 (m, 2 H), 2.75 (q, J=7.5 Hz, 2 H), 2.39 (s, 3 H), 1.81-1.91 (m, 2 H), 1.32 (t, J=7.5 Hz, 3 H), 1.04 (t, J=7.3 Hz, 3 H); $^{13}$C NMR (CDCl$_3$): δ 173.8, 173.7, 168.9, 164.0, 157.4, 150.2, 137.7, 131.7, 131.5, 128.3, 126.6, 122.3, 120.5, 118.7, 74.2, 70.0, 62.1, 42.3, 40.3, 23.0, 22.8, 16.5, 14.8, 13.9.

Example 3

(S)—N-(3-(2-Ethyl-4-(5-(2-isopropylpyridin-4-yl)-1,2,4-oxadiazol-3-yl)-6-methylphenoxy)-2-hydroxypropyl)-2-hydroxyacetamide

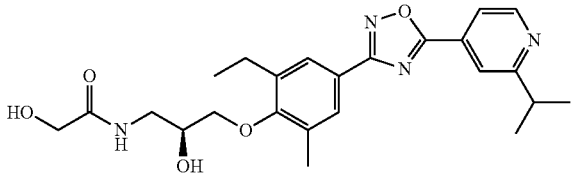 [SMILES: CCc1cc(-c2noc(-c3ccnc(C(C)C)c3)n2)cc(C)c1OC[C@@H](O)CNC(=O)CO]

Prepared in analogy to Example 1. Beige solid; LC-MS: $t_R$=0.71 min, [M+1]$^+$=455.20; $^1$H NMR (CDCl$_3$): δ 8.75 (d, J=5.1 Hz, 1 H), 7.93 (s, 1 H), 7.81-7.86 (m, 3 H), 7.37 (t, J=5.8 Hz, 1 H), 4.16-4.24 (m, 3 H), 3.82-3.92 (m, 3 H), 3.78 (ddd, $J_1$=14.0 Hz, $J_2$=6.5 Hz, $J_3$=3.1 Hz, 1 H), 3.48-3.57 (m, 1 H), 3.22 (hept, J=7.0 Hz, 1 H), 2.73 (q, J=7.5 Hz, 2 H), 2.37 (s, 3 H), 1.40 (d, J=6.9 Hz, 6 H), 1.30 (t, J=7.5 Hz, 3 H); $^{13}$C NMR (CDCl$_3$): δ 174.0, 173.4, 169.04, 168.99, 157.4, 150.2, 137.7, 131.70, 131.67, 128.4, 126.7, 122.4, 118.9, 118.6, 74.1, 70.1, 62.2, 42.3, 36.5, 22.9, 22.5, 16.5, 14.8.

Example 4

(S)—N-(3-(2-ethyl-4-(5-(2-butylpyridin-4-yl)-1,2,4-oxadiazol-3-yl)-6-methylphenoxy)-2-hydroxypropyl)-2-hydroxyacetamide

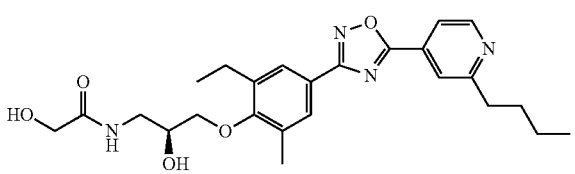 [SMILES: CCCCc1cc(-c2nc(-c3cc(C)c(OC[C@@H](O)CNC(=O)CO)c(CC)c3)no2)ccn1]

Prepared in analogy to Example 1. Beige solid; LC-MS: $t_R$=0.75 min, [M+1]$^+$=469.19; $^1$H NMR (CDCl$_3$): δ 8.77 (d, J=5.1 Hz, 1 H), 7.93 (s, 1H), 7.82-7.89 (m, 3 H), 7.24 (t br, J=5.7 Hz, 1 H), 4.18-4.25 (m, 3 H), 3.90 (dd, $J_1$=9.6 Hz, $J_2$=4.7 Hz, 1 H), 3.85 (dd, $J_1$=9.5 Hz, $J_2$=6.1 Hz, 1 H), 3.79 (ddd, $J_1$=14.2 Hz, $J_2$=6.7 Hz, $J_3$=3.3 Hz, 1 H), 3.49-3.57 (m, 1 H), 3.15 (s br, 2 H), 2.91-2.98 (m, 2 H), 2.74 (q, J=7.5 Hz, 2 H), 2.38 (s, 3 H), 1.76-1.85 (m, 2 H), 1.40-1.50 (m, 2 H), 1.31 (t, J=7.5 Hz, 3 H), 0.99 (t, J=7.3 Hz, 3 H); $^{13}$C NMR (CDCl$_3$): δ 174.0, 173.2, 169.0, 164.3, 157.4, 150.3, 137.7, 131.7, 131.5, 128.4, 126.7, 122.4, 120.5, 118.7, 74.1, 70.2, 62.2, 42.3, 38.1, 31.9, 22.9, 22.5, 16.5, 14.8, 13.9.

Example 5

(S)—N-(3-(2-Ethyl-4-(5-(2-isobutylpyridin-4-yl)-1,2,4-oxadiazol-3-yl)-6-methylphenoxy)-2-hydroxypropyl)-2-hydroxyacetamide

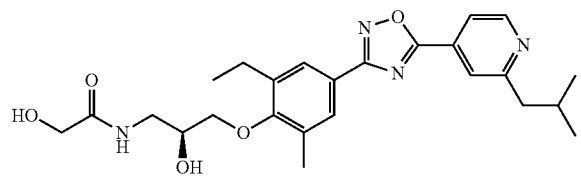 [SMILES: CCc1cc(-c2noc(-c3ccnc(CC(C)C)c3)n2)cc(C)c1OC[C@@H](O)CNC(=O)CO]

Prepared in analogy to Example 1. Beige wax; LC-MS: $t_R$=0.73 min, [M+1]$^+$=469.21; $^1$H NMR (CDCl$_3$): δ 8.79 (d, J=5.1 Hz, 1 H), 7.85-7.91 (m, 4 H), 7.14 (t, J=5.6 Hz, 1 H), 4.17-4.26 (m, 3 H), 3.76-3.94 (m, 3 H), 3.61 (s br, 1 H), 3.49-3.58 (m, 1 H), 3.28 (s br, 1 H), 2.82 (d, J=7.2 Hz, 2 H), 2.75 (q, J=7.5 Hz, 2 H), 2.39 (s, 3 H), 2.14-2.28 (m, 1 H), 1.32 (t, J=7.5 Hz, 3 H), 1.00 (d, J=6.6 Hz, 6 H); $^{13}$C NMR (CDCl$_3$): δ 173.9, 173.5, 169.0, 163.4, 157.4, 150.3, 137.7, 131.7, 131.4, 128.4, 126.7, 122.4, 121.2, 118.7, 74.2, 70.1, 62.2, 47.5, 42.3, 29.4, 22.9, 22.4, 16.5, 14.8; LC-HRMS: $t_R$=1.78 min, [M+H]/z=469.2451, found=469.2446.

Example 6

(S)—N-(3-(2-ethyl-4-(5-(2-isopentylpyridin-4-yl)-2,4-oxadiazol-3-yl)-6-methylphenoxy)-2-hydroxypropyl)-2-hydroxyacetamide

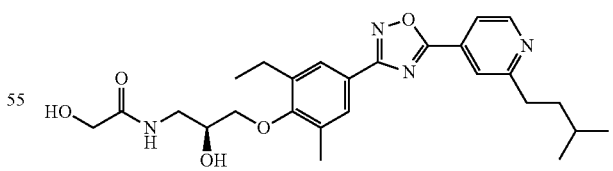

Prepared in analogy to Example 1. White solid; LC-MS: $t_R$=0.92 min, [M+1]$^+$=483.18; $^1$H NMR (CDCl$_3$): δ 8.79 (d, J=5.1 Hz, 1 H), 7.95 (s, 1 H), 7.86-7.90 (m, 3 H), 7.12 (t, J=5.8 Hz, 1 H), 4.17-4.26 (m, 3 H), 3.91 (dd, $J_1$=9.5 Hz, $J_2$=4.8 Hz, 1 H), 3.77-3.88 (m, 2 H), 3.53 (m, 1 H), 2.93-2.99 (m, 2 H), 2.76 (q, J=7.5 Hz, 2 H), 2.40 (s, 3 H), 1.83-1.88 (m, 2 H), 1.66-1.76 (m, 1 H), 1.33 (t, J=7.5 Hz, 3 H), 1.01 (d, J=6.2 Hz, 6 H); $^{13}$C NMR (CDCl$_3$): δ 173.9, 173.4, 169.0, 164.5, 157.5, 150.3, 137.8, 131.7, 131.6, 128.4, 126.7, 122.4, 120.5, 118.7, 74.1, 70.2, 62.2, 46.4, 42.3, 36.4, 28.0, 22.9, 22.5, 16.5, 14.8.

Example 7

(S)—N-(3-(2-ethyl-4-(5-(2-(pentan-3-yl)-pyridin-4-yl)-1,2,4-oxadiazol-3-yl)-6-methylphenoxy)-2-hydroxypropyl)-2-hydroxyacetamide

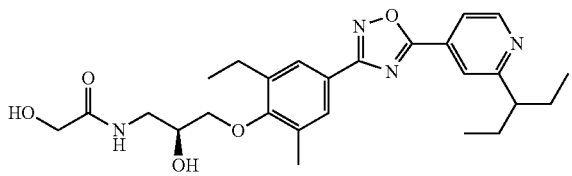 [SMILES: CCc1cc(-c2noc(-c3ccnc(C(CC)CC)c3)n2)cc(C)c1OC[C@@H](O)CNC(=O)CO]

Prepared in analogy to Example 1. Beige wax; LC-MS: $t_R$=0.80 min, [M+1]$^+$=483.27; $^1$H NMR (CDCl$_3$): δ 8.80 (d, J=5.1 Hz, 1 H), 7.81-7.90 (m, 4 H), 7.45 (t, J=5.8 Hz, 1 H), 4.57 (s br, 2 H), 4.16-4.25 (m, 3 H), 3.82-3.92 (m, 2 H), 3.78 (ddd, J$_1$=14.0 Hz, J$_2$=6.5 Hz, J$_3$=3.1 Hz, 1 H), 3.48-3.57 (m, 1 H), 2.68-2.78 (m, 3 H), 2.37 (s, 3 H), 1.74-1.87 (m, 4 H), 1.30 (t, J=7.5 Hz, 3 H), 0.83 (t, J=7.4 Hz, 6 H); $^{13}$C NMR (CDCl$_3$): δ 174.1, 173.4, 169.0, 167.2, 157.4, 150.4, 137.7, 131.7, 131.3, 128.4, 126.7, 122.5, 120.5, 118.8, 74.1, 70.1, 62.2, 51.6, 42.3, 28.2, 22.9, 16.5, 14.8, 12.1; LC-HRMS: $t_R$=1.93 min, [M+H]/z=483.2607. found=483.2601.

Example 8

(S)—N-(3-(2-ethyl-4-(5-(2-cyclopentylpyridin-4-yl)-1,2,4-oxadiazol-3-yl)-6-methylphenoxy)-2-hydroxypropyl)-2-hydroxyacetamide

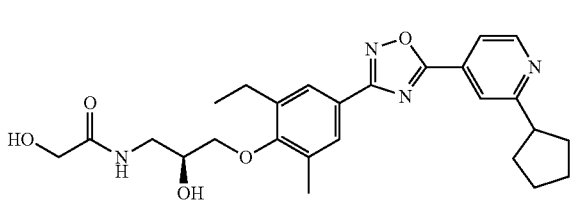 [SMILES: CCc1cc(-c2noc(-c3ccnc(C4CCCC4)c3)n2)cc(C)c1OC[C@@H](O)CNC(=O)CO]

Prepared in analogy to Example 1. White solid; LC-MS: $t_R$=0.78 min, [M+1]$^+$=481.06; $^1$H NMR (CDCl$_3$): δ 8.78 (d, J=5.1 Hz, 1 H), 7.96 (s, 1 H), 7.83-7.88 (m, 3 H), 7.25-7.32 (m, 1 H), 4.17-4.25 (m, 3 H), 3.90 (dd, J$_1$=9.5 Hz, J$_2$=4.5 Hz, 1 H), 3.85 (dd, J$_1$=9.5 Hz, J$_2$=6.0 Hz, 1 H), 3.79 (ddd, J$_1$=14.3 Hz, J$_2$=6.8 Hz, J$_3$=3.3 Hz, 1 H), 3.49-3.58 (m, 1 H), 3.45 (s br, 2 H), 3.29-3.39 (m, 1 H), 2.74 (q, J=7.5 Hz, 2 H), 2.38 (s, 3 H), 2.13-2.27 (m, 2 H), 1.71-1.97 (m, 6 H), 1.31 (t, J=7.5 Hz, 3 H); $^{13}$C NMR (CDCl$_3$): δ 174.1, 173.1, 169.0, 167.5, 157.4, 150.2, 137.7, 131.7, 131.5, 128.4, 126.7, 122.4, 119.5, 118.7, 74.1, 70.2, 62.2, 48.0, 42.3, 33.6, 25.9, 22.9, 16.5, 14.8; LC-HRMS: $t_R$=1.90 min, [M+H]/z=481.2451. found=481.2450.

Example 9

GTPγS Assay to Determine EC$_{50}$ Values

GTPγS binding assays are performed in 96 well microtiter plates (Nunc, 442587) in a final volume of 200 μl, using membrane preparations of CHO cells expressing recombinant human S1P$_1$ receptor or human S1P$_3$ receptor. Assay conditions are 20 mM HEPES (Fluka, 54461), 100 mM NaCl (Fluka, 71378), 5 mM MgCl$_2$ (Fluka, 63064), 0.1% BSA (Calbiochem, 126609), 1 μM GDP (Sigma, G-7127), 2.5% DMSO (Fluka, 41644), 50 pM $^{35}$S-GTPγS (Amersham Biosciences, SJ1320). The pH is 7.4. Test compounds are dissolved and diluted in 100% DMSO and pre-incubated at room temperature for 30 min in 150 μl of the above assay buffer, in the absence of $^{35}$S-GTPγS. After addition of 50 μl of $^{35}$S-GTPγS, the assay is incubated for 1 h at rt. The assay is terminated by transfer of the reaction mixture to a Multiscreen plate (Millipore, MAHFC1H60) using a cell harvester from Packard Biosciences, and the plates are washed with ice-cold 10 mM Na$_2$HPO$_4$/NaH$_2$PO$_4$ (70%/30%), dried, sealed at the bottom and, after addition of 25 μl MicroScint20 (Packard Biosciences, order#6013621), sealed on the top. Membrane-bound $^{35}$S-GTP-γS is measured with a TopCount from Packard Biosciences.

EC$_{50}$ is the concentration of agonist inducing 50% of the maximal specific $^{35}$S-GTPγS binding. Specific binding is determined by subtracting non-specific binding from maximal binding. Maximal binding is the amount of cpm bound to the Multiscreen plate in the presence of 10 μM of SIP. Non-specific binding is the amount of binding in the absence of an agonist in the assay.

Agonistic activities (EC$_{50}$ values) of all exemplified compounds have been measured and are in the range of 0.1 to 5.1 nM with an average of 1.3 nM on S1P$_1$ receptor. EC$_{50}$ values on S1P$_3$ receptor are in the range of 700 and 9950 with an average of 2641 nM. Agonistic activities are displayed in Table 3.

TABLE 3

| Compound of Example | R$^1$ | R$^2$ | EC$_{50}$ [nM] S1P$_1$ | EC$_{50}$ [nM] S1P$_3$ |
|---|---|---|---|---|
| 1 | ethyl | | 2.1 | 9950 |
| 2 | n-propyl | | 0.7 | 1120 |

TABLE 3-continued

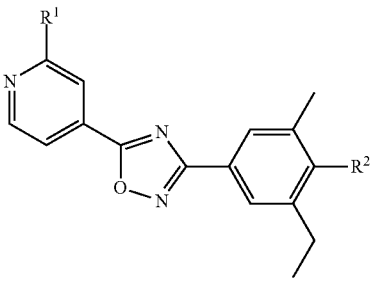

| Compound of Example | R$^1$ | R$^2$ | EC$_{50}$ [nM] S1P$_1$ | EC$_{50}$ [nM] S1P$_3$ |
|---|---|---|---|---|
| 3 | isopropyl | —O—CH$_2$—CH(OH)—CH$_2$—NH—C(O)—CH$_2$OH | 0.3 | 3940 |
| 4 | n-butyl | —O—CH$_2$—CH(OH)—CH$_2$—NH—C(O)—CH$_2$OH | 1.8 | 700 |
| 5 | isobutyl | —O—CH$_2$—CH(OH)—CH$_2$—NH—C(O)—CH$_2$OH | 0.2 | 757 |
| 6 | isopentyl | —O—CH$_2$—CH(OH)—CH$_2$—NH—C(O)—CH$_2$OH | 5.1 | 2600 |
| 7 | pent-3-yl | —O—CH$_2$—CH(OH)—CH$_2$—NH—C(O)—CH$_2$OH | 0.1 | 1340 |
| 8 | cyclopentyl | —O—CH$_2$—CH(OH)—CH$_2$—NH—C(O)—CH$_2$OH | 0.1 | 736 |

Example 10

Assessment of In Vivo Efficacy

The efficacy of the compounds of Formula (I) is assessed by measuring the circulating lymphocytes after oral administration of 3 to 30 mg/kg of a compound of Formula (I) to normotensive male Wistar rats. The animals are housed in climate-controlled conditions with a 12 h-light/dark cycle, and have free access to normal rat chow and drinking water. Blood is collected before and 3, 6 and 24 h after drug administration. Full blood is subjected to hematology using Advia Hematology system (Bayer Diagnostics, Zürich, Switzerland).

All data are presented as mean±SEM. Statistical analyses are performed by analysis of variance (ANOVA) using Statistica (StatSoft) and the Student-Newman-Keuls procedure for multiple comparisons. The null hypothesis is rejected when $p<0.05$.

As an example, Table 4 shows the effect on lymphocyte counts 6 h after oral administration of 10 mg/kg of a compound of the present invention to normotensive male Wistar rats as compared to a group of animals treated with vehicle only. Lymphocyte counts 6 h after oral administration have been measured for 2 out of 8 exemplified compounds and are in the range of −71% to −73% with an average of −72%.

TABLE 4

| Compound of Example | Lymphocyte counts |
|---|---|
| 7 | −71% |
| 8 | −73% |

The invention claimed is:

1. A compound of Formula (I),

Formula (I)

wherein
R$^1$ represents C$_{2-5}$-alkyl or cyclopentyl; and
R$^2$ represents —OCH$_2$—CH(OH)—CH$_2$—NHCO—CH$_2$OH;
or a salt thereof.

2. A compound according to claim 1, wherein R$^1$ represents ethyl, n-propyl, isopropyl, n-butyl, isobutyl, isopentyl, pent-3-yl, or cyclopentyl, or a salt thereof.

3. A compound according to claim 1, wherein R$^1$ represents n-propyl, isopropyl, isobutyl, or cyclopentyl, or a salt thereof.

4. A compound according to claim 1, wherein R$^1$ represents cyclopentyl, or a salt thereof.

5. A compound according to claim 1, wherein the stereocenter of the
R$^2$ group —OCH$_2$—CH(OH)—CH$_2$—NHCO—CH$_2$OH
is in the S-configuration, or a salt thereof.

6. A compound according to claim 1 selected from the group consisting of:
(S)—N-(3-(2-ethyl-4-(5-(2-ethylpyridin-4-yl)-1,2,4-oxadiazol-3-yl)-6-methyl-phenoxy)-2-hydroxypropyl)-2-hydroxyacetamide;
(S)—N-(3-(2-ethyl-4-(5-(2-propylpyridin-4-yl)-1,2,4-oxadiazol-3-yl)-6-methyl-phenoxy)-2-hydroxypropyl)-2-hydroxyacetamide;
(S)—N-(3-(2-ethyl-4-(5-(2-isopropylpyridin-4-yl)-1,2,4-oxadiazol-3-yl)-6-methylphenoxy)-2-hydroxypropyl)-2-hydroxyacetamide;

(S)—N-(3-(2-ethyl-4-(5-(2-butylpyridin-4-yl)-1,2,4-oxadiazol-3-yl)-6-methylphenoxy)-2-hydroxypropyl)-2-hydroxyacetamide;

(S)—N-(3-(2-ethyl-4-(5-(2-isobutylpyridin-4-yl)-1,2,4-oxadiazol-3-yl)-6-methylphenoxy)-2-hydroxypropyl)-2-hydroxyacetamide;

(S)—N-(3-(2-ethyl-4-(5-(2-isopentylpyridin-4-yl)-1,2,4-oxadiazol-3-yl)-6-methylphenoxy)-2-hydroxypropyl)-2-hydroxyacetamide;

(S)—N-(3-(2-ethyl-4-(5-(2-(pentan-3-yl)-pyridin-4-yl)-1,2,4-oxadiazol-3-yl)-6-methylphenoxy)-2-hydroxypropyl)-2-hydroxyacetamide; and (S)—N-(3-(2-ethyl-4-(5-(2-cyclopentylpyridin-4-yl)-1,2,4-oxadiazol-3-yl)-6-methylphenoxy)-2-hydroxypropyl)-2-hydroxyacetamide;

or a salt of any such compound.

7. A compound according to claim 1 which is (S)—N-(3-(2-ethyl-4-(5-(2-cyclopentylpyridin-4-yl)-1,2,4-oxadiazol-3-yl)-6-methylphenoxy)-2-hydroxyproplyl)-2-hydroxyacetamide or a salt thereof.

8. A pharmaceutical composition comprising
a compound according to claim 1, in free or pharmaceutically acceptable salt form, and
a pharmaceutically acceptable carrier.

9. A compound according to claim 1 which is (S)—N-(3-(2-ethyl-4-(5-(2-ethylpyridin-4-yl)-1,2,4-oxadiazol-3-yl)-6-methyl-phenoxy)-2-hydroxypropyl)-2-hydroxyacetamide or a salt thereof.

10. A pharmaceutical composition comprising
a compound according to claim 7, in free or pharmaceutically acceptable salt form, and
a pharmaceutically acceptable carrier.

11. A pharmaceutical composition comprising
a compound according to claim 9, in free or pharmaceutically acceptable salt form, and
a pharmaceutically acceptable carrier.

* * * * *